United States Patent [19]

Schrier

[11] 4,221,414
[45] Sep. 9, 1980

[54] CONTACT LENS INSERTION AND REMOVAL DEVICE

[75] Inventor: Israel Schrier, Irondequoit, N.Y.

[73] Assignee: Bausch & Lomb Incorporated, Rochester, N.Y.

[21] Appl. No.: 946,250

[22] Filed: Sep. 27, 1978

[51] Int. Cl.² ............................................. A61F 9/00
[52] U.S. Cl. ............................................. 294/1 CA
[58] Field of Search ............... 294/1 CA, 8.5, 25, 33, 294/99 R; 81/43; 128/303 R, 321, 354; 206/5.1

[56] References Cited

U.S. PATENT DOCUMENTS

| 907,347 | 12/1908 | Hart | 81/43 |
|---|---|---|---|
| 1,889,475 | 11/1932 | Henkel | 81/43 |
| 3,490,806 | 1/1970 | Lopez-Calleja et al. | 294/1 CA |
| 4,082,339 | 4/1978 | Ross | 294/1 CA |
| 4,088,359 | 5/1978 | Buchanan | 294/1 CA |
| 4,093,291 | 6/1978 | Schurgin | 294/1 CA |
| 4,126,345 | 11/1978 | List | 294/1 CA |

Primary Examiner—Johnny D. Cherry
Attorney, Agent, or Firm—Frank C. Parker; John S. Norton

[57] ABSTRACT

A device for the insertion and removal of soft contact lenses comprises a bifurcated member having a pair of flexible members extending from the main body and contact lens gripping surfaces attached to the ends of each of the flexible members. The angular tips are constructed and shaped at the precise angle necessary, so that when placed against a contact lens, the lens may be flexed and removed from the eye, or, inversely, easily placed on the eye.

10 Claims, 3 Drawing Figures

CONTACT LENS INSERTION AND REMOVAL DEVICE

BACKGROUND OF THE INVENTION

This invention relates to an apparatus for the insertion and removal of contact lenses; particularly soft contact lenses. As is well known in the contact lens art, proper care of contact lenses includes the insertion and removal of the lenses without risking contamination by foreign substances such as those carried by the fingers of the person inserting the lenses. In order to provide such care, numerous contact lens insertion devices have been developed in the past. Examples of such devices include:

| U.S. Pat. Nos. | Date of Issue | Inventor | Title |
| --- | --- | --- | --- |
| 4,093,291 | 6/6/78 | Herbert L. Schurgin | Contact lens Application and Removal instrument |
| 4,088,359 | 5/9/78 | Richard S. Buchanan, Jr. | Contact lens Inserter |
| 4,082,339 | 4/4/78 | Joseph Roth | Soft contact lens Insertion and removal Instrument |
| 3,628,824 | 12/21/71 | David Leuw | Implement for grasping Small objects |
| 3,177,874 | 4/13/65 | J. D. Spriggs | Contact lens Applicator |
| 3,115,360 | 12/24/63 | R. S. Witcoff | Resilient gripping Device |
| 2,406,393 | 8/27/46 | E. A. Neugass | Tweezer implement and the like |
| 1,250,422 | 12/18/17 | G. J. Bohlman | Paper tong |
| 987,173 | 3/21/11 | F. Sale | Nippers |

While several of these devices can be used to remove a contact lens from the eye, none of them are particularly designed to utilize a pair of lens gripping members to engage, flex, hold and remove soft contact lens from the eye.

For example, it has been found in the past that suction cups are not useful in removing soft contact lenses because they tend to pull the lens away from the eye rather than releasing the surface tension between the lens and the lacrymal fluid of the eye. As a result, corneal cells may be damaged.

It has also been found that the cornea is too sensitive in the majority of cases to allow removal of the lens without increasing the possibility of causing injury, however slight, to the eye. Therefore, it is now common procedure to move the lens to the scleral portion of the eye. A problem exists, however, in that the user then does not have clear vision needed to remove the lens once the lens is moved to the sclera.

Further complications arise when fingers are used to remove the lens from the eye. For example, long fingernails tend to scratch the eye; users with rough fingers tend to injure the eye and/or abrade the lens, and in some cases the fingers may be too large for sufficient dexterity to remove the lens. A consummate problem is the lack of cleanliness of fingers, which tends to contaminate the lens.

An additional problem with most contact lens insertion devices is that they do not facilitate kinesthesis (the sense whose end organs lie in the muscles, tendons and joints and are stimulated by bodily movements and tensions; the muscle sense); Webster's New International Dictionary, 2nd Edition. In other words, most of these devices do not allow an accurate perception of where the lens is in relationship to the eye. Such perception is in addition to visual perception of the position of the lens in relation to the eye.

Accordingly, it is an object of the present invention to provide a device for insertion and removal of soft contact lenses from the eye of the user in which the suction between the lens and the eye may be broken, and the lens thereby easily removed from the eye;

to provide such devices in a form which is easy and inexpensive to manufacture;

to provide such devices from a material which is soft so as not to injure the eye and sterilizable so as not to contaminate the lens; and to provide a device which tends to maximize kinesthesis during insertion and removal of the lens from the eye.

SUMMARY OF THE INVENTION

The present invention is an improved apparatus for inserting and removing contact lenses from the eye of the user. The invention comprises a bifuricated member member with a pair of flexible branches extending therefrom. At the end of each of the flexible branches is an angular tip which is adapted in shape and position so that, when placed against the contact lens on the eye, the lens may be flexed (bending the lens so as to raise it up enough to let air underneath it reach the cornea). As a result, upon such flexing, the surface tension between the lens and the eye is broken and the lens may be removed. Additionally, the angular tips are positioned to easily allow for gripping and holding of the contact lens. Placement of the lens onto, or removal from, the eye of the user is thereby easily facilitated.

One of the key aspects of the invention is that the flexible branches are designed so that the fingertips of the user are closely proximate to the angular contact lens gripping tips. As a result, the distance between the user's fingertips, the contact lens and the eye is minimized during insertion and removal of the contact lens. Consequently, kinesthesis (the ability of the person to perceive spatial relationships of the parts of his body without requiring visual perception) is maximized.

One of the key inventive aspects of the device is construction of the tips of the flexible branches in a manner which enables the flexing of the contact lens while on the eye. This flexing breaks the surface tension between the lens and the eye and allows for easy removal of the lens. Basically, the angular tips have two features which cause such flexing. To begin with the tips are constructed in a wedge shape having relatively sharp edges. The inside edges of the tips pinch the edge of the lens so that the surface tension between the lens and the eye may be broken and the lens easily removed from the eye. Inversely, the lens may also easily be placed on the eye. A second feature is the use of substantially flat surfaces on each tip which are, juxtaposed at an angle of approximately 150°±5° to each other. As a result, when placed against the lens, these substantially flat surfaces tend to hold the lens as they are brought together and the lens is removed from the eye, folding the lens in half toward the main body member.

As an additional feature of the invention, the angular tip may also be inclined at an approximate angle of 15°±5° from front to back in order to utilize this device from below the eye. As a result, a mirror may be used to facilitate insertion or removal of the lens from the eye, without the hands of the user impairing vision into the mirror.

The invention may further include an annular inserter ring which would, in a preferred embodiment, comprise a collar which extends from the main body member at approximately a 30° angle. An aperture is bored through the collar. This aperture may be bored through the main body member as well in order to allow viewing through the ring into a mirror, which facilitates placement of the lens on the eye. The collar may also include a bevelled edge which would engage and cradle the contact lens thereon. In a preferred embodiment, the bevelled edge would be radiused to closely correspond to the anterior curve of the contact lens specified. As a result, the lens is held in place by the surface tension between the lens, the contact lens soaking solution thereon and the inserter ring.

In a preferred embodiment the device is constructed of a material which is flexible and soft in order to resist injury to the eye. A present preferred material is a thermoplastic elastomer such as Kraton TM which is sterilizable, is F.D.A. approved, has desirable friction properties to hold the lens, is injection moldable and is inexpensive. Kraton TM is a product of Shell Chemical Company and is described in Brochure No. SC: 68–77 published in March, 1977.

DETAILED DESCRIPTION OF THE DRAWINGS

Figure 2:
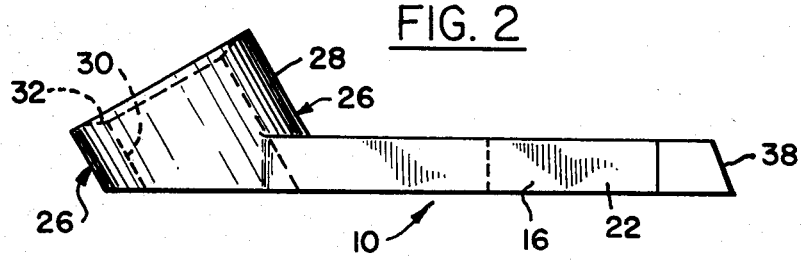
FIG. 2 of the drawings is a side view of the contact lens insertion and removal device of FIG. 1, showing in particular a contact lens inserter ring.

While this invention is susceptible of embodiments in many different forms, there is shown in the drawings, and will herein be described in detail, specific embodiments, with the understanding that the present disclosure is to be considered as an exemplification of the principles of the invention and is not intended to limit the invention to the embodiments illustrated.

Figure 1:
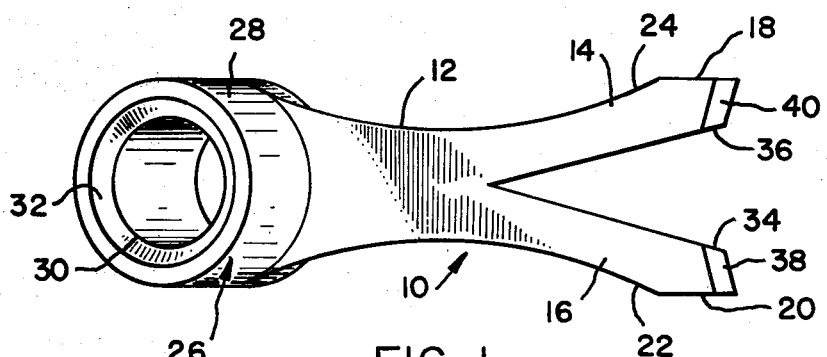
FIG. 1 of the drawings is a top perspective view of an improved contact lens insertion and removal device.

Improved contact lens insertion and removal device 10, as shown in FIG. 1, comprises a bifurcated member 12 with flexible members or branches 14 and 16 extending therefrom. At the end of flexible members 14 and 16 are angular tips 18 and 20, respectively which are adapted in shape and position so that when placed against a contact lens on the eye, the lens may be flexed, (puckered at its edges). As a result, the surface tension between the lens and the eye is broken and the lens may be removed. Similarly, the lens may be easily gripped for insertion into the eye.

One of the means which enables easy insertion and removal of contact lenses with applicant's device are finger gripping areas 22 and 24, which are depressions, as best seen in FIG. 1, integrally formed in flexible members 14 and 16, respectively. Generally, the tips of the user's thumb and forefinger will engage the gripping areas 22 and 24 closely proximate to angular contact lens gripping tips 18 and 20. The distance between the user's fingertips, the contact lens and the eye are minimized during insertion and removal making it easier to manipulate the lens.

An additional feature of the invention is inserter ring 26 which is attached approximately at a 30° angle to main body member 12 at the end opposite the gripping members 14 and 16. The positioning of inserter ring 26 facilitates insertion of contact lenses to the eye. The inserter ring 26 consists of collar 28 which extends away from main body member 12. The collar 28 has an aperture 30 which has an interior bevelled edge 32 for cradling the contact lens. Collar 28 must be wide enough to properly cradle the lens, but not so large as to interfere with the eyelid during insertion. It has been found that if collar 28 has a diameter no greater than 1 mm less than the contact lens to be inserted, and aperture 30 is approximately ½ to 2 millimeters smaller in diameter than the lens, the lens may be properly cradled and yet easily removed. Interior bevel 32 is radiused to closely correspond to the anterior curve of a contact lens. As a result, when the lens is placed against inserter ring 26, surface tension between the contact lens soaking solution and the lens and inserter ring 26 is sufficient to hold the lens on the inserter ring 26. However, the lens may be easily released when placed against the eye due to the greater surface tension between the lens and the large amount of lacrymal fluid on the eye.

Figure 3:
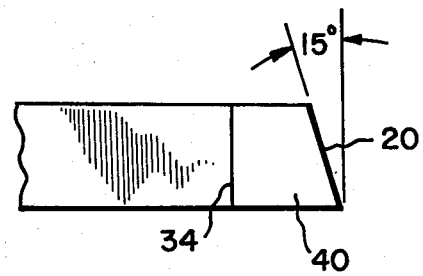
FIG. 3 of the drawings is an enlarged partial side view of a flexible member as shown in FIG. 1.

One aspect of the device is the construction of angular contact lens gripping tips 18 and 20 of flexible members 14 and 16, respectively, in a manner which enables the flexing of the contact lens while on the eye. This flexing breaks the surface tension between the lens and the eye and allows easy removal. In order to allow such flexing, angular tips 18 and 20, as shown in FIGS. 1 and 3, are constructed in a wedge shape having relatively sharp but non-damaging edges. Inside edges 34 and 36 of flexible branches 14 and 16, respectively, are used to grip the lens with sufficient pressure to flex (or pucker) it so that the surface tension between the lens and the eye is broken and the lens may be easily removed. Angular contact lens gripping tips 18 and 20 have flat surfaces 38 and 40 which are juxtaposed at an angle of approximately 150°±5° from each other. These flat surfaces 38 and 40 tend to hold the lens as they are brought together thereby folding the lens in half between branches 14 and 16. As a result, the lens may be easily removed from the eye.

As an additional feature, angular tip 20 as shown in FIG. 3 [and angular tip 18 (not shown)] is inclined at an angle of approximately 15° from the vertical or, in other words, from front to back. This allows the device to be introduced to the eye angularly from a position somewhat below the eye thereby allowing removal of the lens without obstructing the vision of the user. As a result, a mirror may be used to facilitate removal of a lens from the eye.

As shown in FIG. 2 of the drawings, annular inserter ring 26 comprises collar 28 extending away from bifurcated member 12 at an angle of approximately 30°. An aperture 30 is bored through the collar 28 and may be bored through the main body member 12 as well in order to allow viewing through annular inserter ring 26 into a mirror while placing the lens on the eye. Also shown in FIG. 2 is an interior bevel 32 which is formed on aperture 30 at the upper surface of inserter ring 26. The bevel 32 has a radius closely corresponding to the anterior curve of a contact lens. As a result, when the lens is placed on annular inserter ring 26 it seats on the radiused bevel 32 and creates surface tension between the lens which has contact lens soaking solution thereon, and the bevel 32 of inserter ring 26 holds the lens on the inserter ring 26.

In a preferred embodiment, contact lens insertion device 10 is constructed of a material which is flexible and soft in order to resist injury to the eye. An ideal material for such a device is thermoplastic elastomer.

The foregoing description and drawings merely explain and illustrate the invention and the invention is not limited thereto, except insofar as the appended claims are so limited as those skilled in the art who have the disclosure before them will be able to make modifications and variations therein without departing from the scope of the invention.

I claim:

1. A device for aiding a user of soft contact lenses in introducing and removing a soft contact lens from an eye, comprising:

a bifurcated member having longitudinal and vertical axes the two branches of which are flexible and extend angularly away from the point of division and terminate in flexible contact lens gripping surfaces oblique to both the longitudinal and vertical axis and supportive of the anterior surface of the lens to aid the user in introducing the lens to the eye at the proper angle and to raise the edge of the lens from the eye when placed against the lens by squeezing the flexible branches together to break the surface tension between the lens and the eye to provide for easy removal of the lens from the eye.

2. The invention according to claim 1 in which said flexible branches include finger gripping depressions formed closely proximate to said contact lens gripping surfaces so as to maximize kinesthesis during insertion and removal of the lens thereby facilitating such insertion and removal.

3. The invention according to claim 1, further including:

inserter ring means formed on said bifurcated member for receiving and carrying a soft contact lens and angularly disposed on said main body member so as to facilitate insertion of said contact lens into the eye of the user.

4. The invention according to claim 3 in which said inserter ring means comprises:

a circular collar extending angularly away from said bifurcated member, said circular collar containing an aperture therein, said aperture having an interior bevelled edge which is radiused to closely correspond to the anterior surface of the lens for cradling the contact lens thereon during insertion of the lens to the eye.

5. The invention according to claim 4 in which said circular collar has an outside diameter no larger than 1 mm less than the contact lens to be inserted.

6. The invention according to claim 1 in which said contact lens gripping surfaces comprise wedge shaped members formed on the ends of said flexible gripping surfaces, the inner edges of said wedge shaped members being effective to flex the edge of the lens and raise it from the eye so as to break the surface tension between the contact lens and the eye whereby the contact lens may be easily introduced to or removed from the eye.

7. The invention according to claim 6 in which said contact lens gripping surfaces comprise:

a pair of juxtaposed substantially flat surfaces, said surfaces being positioned at an angle of approximately 150°±5° from each other so as to enable the folding of said contact lens between said gripping surfaces during removal and the holding therebetween during insertion to the eye.

8. The invention according to claim 1 in which said contact lens gripping surfaces are inclined at an angle of approximately 15°±5° from front to back in order to utilize said device from below the eye thereby allowing insertion or removal of the lens without obstructing the vision of the user whereby a mirror may be utilized to facilitate said insertion or removal.

9. The invention according to claim 1 in which said device is constructed from thermoplastic elastomer so as to be flexible in use, soft to resist injury to the eye, and sterilizable.

10. A device for aiding a user of soft contact lenses in introducing and removing a soft contact lens from an eye, comprising:

a bifurcated member the two branches of which are flexible, said branches extending angularly away from the point of division and terminating in flexible contact lens gripping surfaces, said surfaces being angled toward each other and the point of division and further being inclined toward the point of division, said contact lens gripping surfaces being supportive of the anterior surface of said contact lens to aid the user in introducing the lens to the eye at the proper angle and to raise the edge of the lens from the eye when placed against the lens by squeezing the flexible branches together to break the surface tension between the lens and the eye to provide for easy removal of the lens from the eye.

* * * * *